(12) United States Patent
Bieg

(10) Patent No.: US 10,159,436 B2
(45) Date of Patent: Dec. 25, 2018

(54) METHOD AND APPARATUS FOR RECOGNIZING FATIGUE AFFECTING A DRIVER

(71) Applicant: Robert Bosch GmbH, Stuttgart (DE)

(72) Inventor: Hans-Joachim Bieg, Weil Im Schoenbuch (DE)

(73) Assignee: ROBERT BOSCH GMBH, Stuttgart (DE)

( * ) Notice: Subject to any disclaimer, the term of this patent is extended or adjusted under 35 U.S.C. 154(b) by 21 days.

(21) Appl. No.: 15/418,110

(22) Filed: Jan. 27, 2017

(65) Prior Publication Data

US 2017/0215784 A1  Aug. 3, 2017

(30) Foreign Application Priority Data

Feb. 2, 2016 (DE) .................. 10 2016 201 531

(51) Int. Cl.
| | |
|---|---|
| *A61B 5/18* | (2006.01) |
| *A61B 3/00* | (2006.01) |
| *A61B 3/113* | (2006.01) |
| *A61B 3/14* | (2006.01) |
| *A61B 5/16* | (2006.01) |

(52) U.S. Cl.
CPC .............. *A61B 5/18* (2013.01); *A61B 3/0025* (2013.01); *A61B 3/113* (2013.01); *A61B 3/145* (2013.01); *A61B 5/163* (2017.08)

(58) Field of Classification Search
CPC  A61B 5/18; A61B 3/113; A61B 3/145; A61B 3/0025
See application file for complete search history.

*Primary Examiner* — Jack Dinh
(74) *Attorney, Agent, or Firm* — Norton Rose Fulbright US LLP; Gerard Messina

(57) ABSTRACT

A method is described for recognizing fatigue, the method comprising an ascertaining step, a determining step, and a comparing step. In the ascertaining step a first saccade and at least one further saccade of an eye movement of a person are ascertained using a gaze direction signal that models the eye movement. In the determining step, a first data point representing a first amplitude of the first saccade and a first peak velocity of the first saccade, and at least one further data point representing a further amplitude of the further saccade and a further peak velocity of the further saccade, are determined using the gaze direction signal. In the comparing step, the first data point and at least the further data point are compared with a saccade model. The person is recognized as fatigued if the data points have a predetermined relationship to a confidence region of the saccade model.

24 Claims, 3 Drawing Sheets

METHOD AND APPARATUS FOR RECOGNIZING FATIGUE AFFECTING A DRIVER

FIELD OF THE INVENTION

The present invention proceeds from an apparatus or a method. A computer program is also a subject of the present invention.

BACKGROUND INFORMATION

In a vehicle, an eye monitoring system can be used, for example, to track a projection region of a field of view display of an eye position of a viewer. Blinking of the eyes can also be monitored by way of the eye monitoring system. Conclusions as to fatigue affecting the viewer can be drawn by way of the blinking.

SUMMARY

In light of the above, what is presented with the approach presented here is a method for recognizing fatigue, furthermore an apparatus that uses that method, and lastly a corresponding computer program, according to the main claims. Advantageous refinements and improvements to the apparatus indicated in the independent claim are possible by way of the features set forth in the dependent claims.

Blinking occurs in part as a reflex. External influences are therefore often the cause of blinking. Blinking can occur, for example, in response to dazzling. Blinking can likewise occur in response to a draft. Monitoring of blinking along therefore does not allow a reliable conclusion as to a person's fatigue.

With the approach presented here, a movement of at least one eye is additionally evaluated in order to draw conclusions as to the person's fatigue. The movement of the eye can be distinguished in general at least as a fixation portion and a saccadic portion. The saccadic portion is made up of a rapid eye movement called a "saccade." Here the saccades are evaluated. A saccade occurs, for example, in order to switch between two objects being viewed. A slow eye movement, on the other hand, occurs, for example, when a moving object is being tracked.

A correlation exists between a movement velocity of the eye during a saccade and a magnitude of the saccade. The "magnitude" can be understood here as an angle between a beginning of the saccade and an end of the saccade. For a person who is not fatigued, this correlation is reproducible with little variance.

As the person becomes fatigued, the variance becomes greater.

A method for recognizing fatigue is presented, the method having the following steps:

ascertaining a first saccade and at least one further saccade of an eye movement of a person, using a gaze direction signal that models the eye movement;

determining a first data point representing a first amplitude of the first saccade and a first maximum velocity of the first saccade, and at least one further data point representing a further amplitude of the further saccade and a further maximum velocity of the further saccade, using the gaze direction signal; and comparing the first data point and at least the further data point with a saccade model, the person being recognized as fatigued if the data points have a predetermined relationship to a confidence region of the saccade model.

A "saccade" can be understood as a movement segment of an eye. The saccade is part of a saccadic period. The saccadic period can be flanked by fixation periods. In the saccade, the eye is moved rapidly from a first angular position into a second angular position. The angle between the first angular position and the second angular position can be referred to as an "amplitude." A maximum angular velocity attained during the saccade can be referred to as a "maximum velocity." A value of the amplitude and a value of the maximum velocity constitute a value pair or a data point. A saccade model numerically models the correlation between the amplitude and the maximum velocity. A confidence region can be referred to as a "tolerance range." The confidence region is delimited by one or two confidence limits. The confidence region can represent a range in a data space, the data space being spanned by the dimensions of the data points. For example, the data space can be spanned in the dimensions of the maximum velocity and the amplitude of the eye movement.

The method can have a step of personalizing the saccade model to the person. Here at least one parameter of the saccade model can be determined using temporally previous (i.e. temporally preceding) data points. Temporally previous or temporally preceding data points that are associated with the person can be used here. The saccade model can be personalized when the person is rested or not fatigued. During personalization, an individual correlation between the amplitude and maximum velocity can be modeled. Personalization allows fatigue affecting the person to be reliably recognized.

The saccade model can be personalized using a predetermined minimum number of data points. With a sufficient data inventory, outliers can be recognized and discarded for personalization. For example, the saccade model can be personalized when 100 data points are collected.

Data points from a predefined time window can be used. For example, the saccade model can be personalized in a predefined time period after a vehicle is started. After starting, the person is with high probability alert or not fatigued.

The person can be recognized as fatigued if a predetermined proportion of the data points lie outside the confidence region. When data points are located outside the confidence region, the variance of the saccades is elevated, which indicates fatigue affecting the person.

The data points can be weighted. For example, data points below the confidence region can be given a greater weight than data points above the confidence region. Data points above the confidence region can indicate defective detection. Weighting allows fatigue to be recognized quickly and reliably.

In the determining step, additional data points of the saccades, representing the amplitude of a saccade and a duration of the saccade, can be determined using the gaze direction signal. The comparing step can be performed using the additional data points. The additional data points can be used to back up the recognition.

A saccade model that is based on the following equation:

$$V_p = V_m(1-e^{-A/C})$$

can be used, where $V_p$ represents the peak velocity, $V_m$ and $C$ represent person-specific parameters, and A represents the amplitude. The person-specific parameters can be adapted in order to personalize the saccade model. The equation can describe a center of the confidence range.

This method can be implemented, for example, in software or hardware or in a mixed form of software and hardware, for example in a control device.

The approach presented here furthermore creates an apparatus that is configured to carry out, control, or implement the steps of a variant of a method presented here in corresponding devices. This variant embodiment of the invention in the form of an apparatus likewise allows the object on which the invention is based to be achieved quickly and efficiently.

The apparatus can have for this purpose: at least one computation unit for processing signals or data; at least one memory unit for storing signals or data; at least one interface to a sensor or to an actuator, for reading in sensor signals from the sensor or for outputting data signals or control signals to the actuator; and/or at least one communication interface for reading in or outputting data that are embedded in a communication protocol. The computation unit can be, for example, a signal processor, a microcontroller, or the like, and the memory unit can be a flash memory, an EPROM, or a magnetic memory unit. The communication interface can be configured to read in or output data wirelessly and/or in wire-based fashion; a communication interface that can read in or output wire-based data can, for example, read in those data from a corresponding data transfer line, or output them into a corresponding data transfer line, electrically or optically.

An "apparatus" can be understood in the present case as an electrical device that processes sensor signals and, as a function thereof, outputs control signals and/or data signals. The apparatus can have an interface that can be configured in hardware- and/or software-based fashion. With a hardware-based configuration the interfaces can be, for example, part of a so-called "system ASIC" that contains a wide variety of functions of the apparatus. It is also possible, however, for the interfaces to be separate integrated circuits or to be made up at least partly of discrete components. With a software-based configuration the interfaces can be software modules that are present, for example, on a microcontroller alongside other software modules.

Also advantageous is a computer program product or computer program having program code that can be stored on a machine-readable medium or memory medium such as a semiconductor memory, a hard-drive memory, or an optical memory, and can be used to carry out, implement, and/or address the steps of the method in accordance with one of the embodiments described above, in particular when the program product or program is executed on a computer or an apparatus.

DETAILED DESCRIPTION

Figure 1:
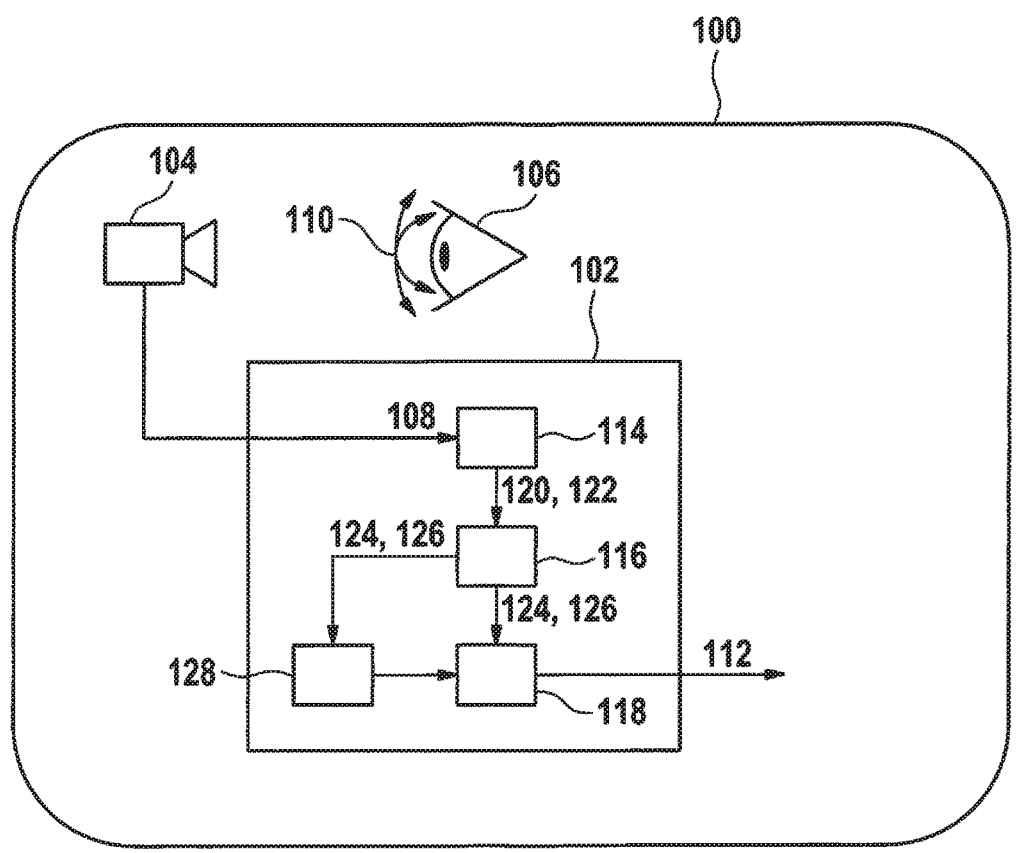
FIG. 1 depicts a vehicle having an apparatus for recognizing fatigue, according to an exemplifying embodiment.

In the description below of favorable exemplifying embodiments of the present invention, identical or similar reference characters are used for the elements that are depicted in the various Figures and function similarly, repeated description of those elements being omitted.

FIG. 1 depicts a vehicle 100 having an apparatus 102 for recognizing fatigue, according to an exemplifying embodiment. Vehicle 100 has an eye detection device 104 that detects at least one eye 106 of a driver of vehicle 100 and models a current gaze direction of eye 106 in a gaze direction signal 108. Gaze direction 108 thus describes an eye movement 110 of eye 106 or eyes 106.

Apparatus 102 for recognizing fatigue is configured to furnish, using gaze direction signal 108, a fatigue signal 112 modeling a degree of fatigue affecting the driver. Apparatus 102 has for that purpose an ascertaining device 114, a determining device 116, and a comparing device 118.

Ascertaining device 114 is configured to ascertain, using gaze direction signal 108, a first saccade 120 and at least one further saccade 122 of eye movement 110. Saccades 120, 122 are rapid eye movements 110. Between two saccades, the driver fixates on an object for at least a brief moment, or eye 106 briefly remains in a gaze direction.

Eye movement 110 changes if the driver is fatigued.

Determining device 116 is configured to determine, using gaze direction signal 108 that models saccades 120, 122, a first data point 124 and at least one further data point 126. First data point 124 models a first amplitude of first saccade 120 and a first peak velocity of first saccade 120. Further data point 126 models a further amplitude of further saccade 122 and a further peak velocity of further saccade 122. The amplitude represents an angle over which the saccade extends. The peak velocity represents a maximum rotation velocity of eye 106 achieved during the saccade.

Comparing device 118 is configured to compare first data point 124 and at least further data point 126 with a saccade model 128. The driver is recognized as fatigued if data points 124, 126 have a predetermined relationship to a confidence region of saccade model 128.

Fatigue signal 112 is furnished if the driver is recognized as fatigued. For example, the driver can be warned. The driver can also be prompted to take a rest.

In an exemplifying embodiment, data points 124, 126 are used to personalize saccade model 128 for the driver. Data points 124, 126 that represent saccades 120, 122 during which the driver was not fatigued are used, for example, for this purpose.

A method for determining fatigue by measuring saccade properties is presented. The method can be executed, for example, on apparatus 102.

An assessment of fatigue affecting a person plays a role in numerous application sectors, in particular in the driving of vehicles 100. Existing methods for fatigue assessment estimate the fatigue state of a person either by measuring the quality of task handling, for example vehicle control quality, or on the basis of physiological features of the person being assessed. Important physiological features for fatigue assessment can be obtained, for example, by surveying eyes 106 of the person being assessed. For example, the person's blinking can be ascertained with the aid of a video-based tracking system 104 (eye tracking system). An accumulation of blinking events, for example, can indicate that a person is fatigued.

A fatigue assessment on the basis of physiological criteria is generally advantageous, but can also result in assessment errors. For example, increased blinking can be due not only to fatigue but also to other circumstances, for example light conditions or air conditions. Further physiological properties can be taken into consideration in order to avoid assessment errors.

The approach presented here describes a method with which further criteria for fatigue assessment in the context of surveying of eyes 106 of the person being assessed can be derived.

A method is described which permits a fatigue assessment based on surveying of properties of rapid eye movements or saccades 120, 122. The method can be used when a tracking system 104 for surveying eyes 106 of the person being assessed is used. It can thus be used for a fatigue assessment or in order to improve existing methods, for example based on blinking.

Figure 2:
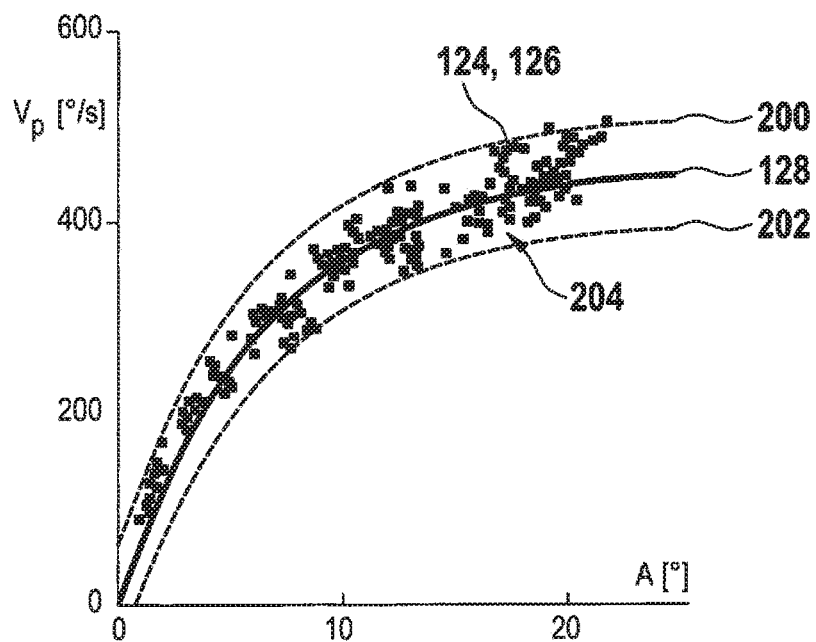
FIG. 2 depicts personalization of a saccade model, according to an exemplifying embodiment.

FIG. 2 illustrates personalization of a saccade model 128 according to an exemplifying embodiment. Saccade model 128 corresponds substantially to the saccade model in FIG. 1. Saccade model 128 is depicted as a function of a peak velocity V versus an amplitude A. The function is depicted in a diagram in which the amplitude A of saccades (in degrees) is plotted on its abscissa and the peak velocity V of the saccades (in degrees per second) is plotted on its ordinate.

A plurality of data points 124, 126 representing saccades of an alert, rested person are depicted in the diagram. Saccade model 128 corresponds substantially to a trend line of a majority of data points 124, 126. In other words, saccade model 128 corresponds to an average of the peak velocity V of the saccades versus their amplitude A.

An upper confidence limit 200 and a lower confidence limit 202 of saccade model 128 are depicted in the diagram. A confidence range 204 of saccade model 128 is located between confidence limits 200, 202. Function 128 is located here at the center of confidence range 204. Confidence range 204 encompasses a specific proportion of all data points 124, 126 of a non-fatigued person. For example, 95% of all data points 124, 126 of a non-fatigued person are located within confidence range 204.

Saccade model 128, upper confidence limit 200, and lower confidence limit 202 are adapted to the actually detected saccades of a person. In other words, saccade model 128 is personalized. It is thus unequivocally evident when data points 124, 126 deviate from confidence range 204 when the person becomes fatigued.

In other words, FIG. 2 shows a typical ratio of saccade amplitude A and peak velocity $V_p$ for an alert viewer. The ratio can be described by a function that is depicted here with a solid line 128, and by a confidence interval 204 that is depicted here with dashed lines 200, 202. Confidence interval 204 can be referred to as a "main sequence."

Figure 3:
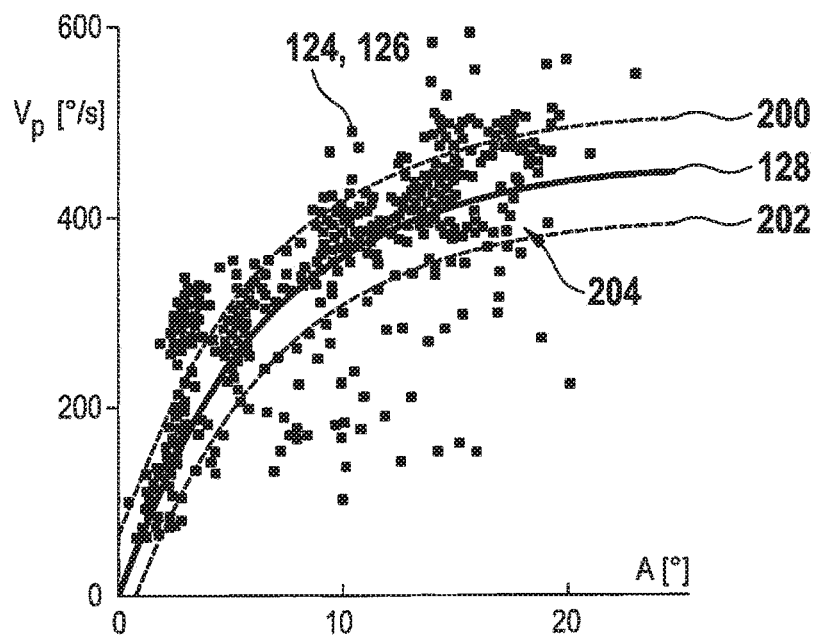
FIG. 3 depicts recognition of fatigue, according to an exemplifying embodiment.

FIG. 3 depicts recognition of fatigue according to an exemplifying embodiment. It shows a saccade model 128, with its confidence limits 200, 202 demarcating confidence range 204, which corresponds substantially to the saccade model in FIG. 2. Data points 124, 126 of saccades of a fatigued person are depicted here. Data points 124, 126 exhibit a greater scatter as compared with the data points of the non-fatigued person in FIG. 2. Here, more than a small proportion of data points 124, 126 are located outside confidence range 204.

In other words, FIG. 3 shows a typical behavior of amplitude A and velocity V for a fatigued viewer. The number of saccades having a ratio outside main sequence 224 is incorporated into the fatigue assessment.

Figure 4:
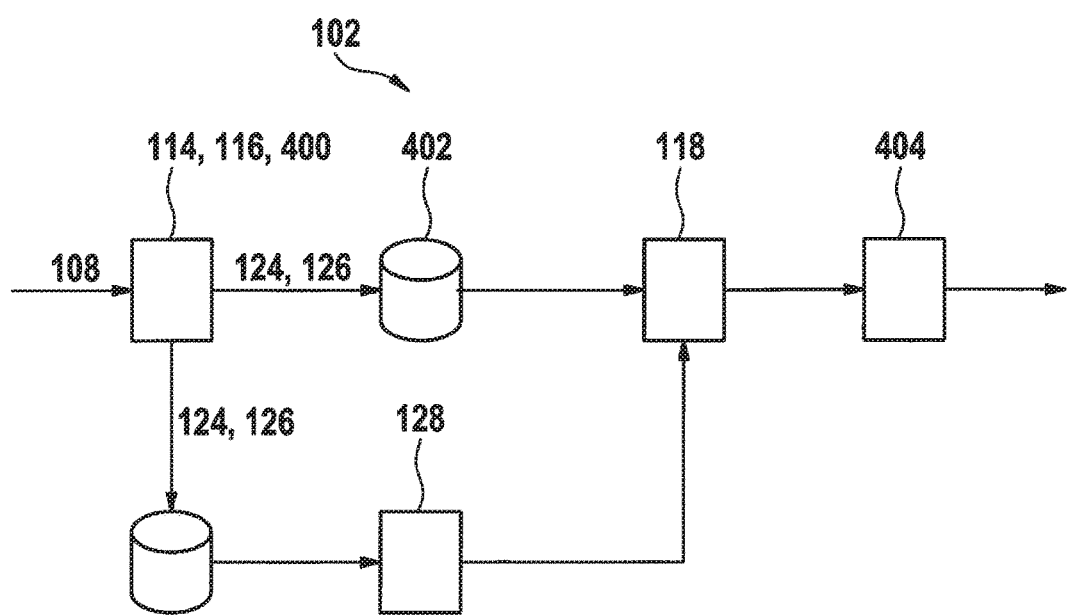
FIG. 4 is a block diagram of an apparatus for recognizing fatigue, according to an exemplifying embodiment.

FIG. 4 is a block diagram of an apparatus 102 for recognizing fatigue, according to an exemplifying embodiment. Apparatus 102 corresponds substantially to the apparatus in FIG. 1. In contrast, devices 114, 116 here are combined into one classification device 400.

The method presented here for fatigue estimation utilizes a biomechanical ratio between the magnitude or amplitude A and the peak velocity V of rapid eye movements, or saccades, of the person being assessed. Saccades are typical eye movements that are performed by every human being approximately every three to four seconds.

A prerequisite for the method presented is that, for example with the aid of a video-based tracking system (eye tracker), a measurement is made of the current gaze direction, i.e. a horizontal and vertical gaze angle, of the person being assessed. The eye tracking system supplies measurements of the current gaze angle at constant time intervals, for example 60 samples per second. The approach presented here is not linked to a specific sampling rate.

In a classifying step executed in classification device 400, the sampled gaze direction signal 108 is subdivided into saccadic and fixation periods. The classification can draw upon previously known methods. As a result of this step, saccades that occur can be extracted from the sampled gaze direction signal and surveyed. The properties 124, 126 surveyed are, in particular, the magnitude or amplitude of the saccades (in degrees) and the peak velocity (in degrees per second).

In a model creation step, a person-specific model 128 is created based on the measured saccade properties 124, 126. Model 128 correlates the amplitude (A) and peak velocity ($V_p$) and can be described by the formula $$V_p = V_m(1 - e^{-A/C})$$

where $V_m$ and C represent person-specific parameters that can be defined based on the recorded data 124, 126 using a statistical regression method. Other formulations of this relationship are possible.

In an exemplifying embodiment, other saccade properties 124, 126 are correlated and serve as a basis for further implementation, for example the ratio of saccade amplitude to saccade duration.

In order to enable a reliable identification of the parameters, a minimum number of measurements can be collected, for example at least 100 measurements. Confidence boxes for the model parameters can also be calculated in accordance with the scatter of the measurement. A confidence region can be described using these boxes. The boxes are selected so that, for example, 95% of data points 124, 126 are located within that region.

The creation of model 128 can occur periodically, and the parameters can be averaged in order to compensate for possible fluctuations in behavior. This ensures that the parameters of model 128 reproduce the gaze behavior of a non-fatigued person.

The creation of model 128 can furthermore be limited to time segments relevant to the task carried out by the person being observed. For example, for ascertaining fatigue affecting a driver a model 128 can be created at the beginning of a journey, in order to increase the probability that the ascertained model parameters model normal, i.e. non-fatigued, behavior.

In a comparing step carried out in comparing device 118, the data of a second data inventory 402 are evaluated. In this step a determination is made as to whether data points 124, 126, i.e. tuples of saccade amplitude and peak velocity, are present in accordance with the expectation of model 128. This is done by checking how many of the data points 124, 126 collected in data inventory 402 are located outside the confidence region defined in model 128.

In an interpreting step performed in an interpreting device 404, the ratio of the number of data points 124, 126 outside the confidence region to the number of data points 124, 126 inside the confidence region is considered in accordance with a predefined tolerance value. If the proportion of data points 124, 126 outside the confidence region is above the tolerance value, for example 20%, this is evaluated as an indication of fatigue, and a corresponding classification is performed.

The consideration in the interpreting step can furthermore be adapted in such a way that data points 124, 126 outside the confidence region that lie above or below the confidence region are interpreted with different weights. For example, data points 124, 126 below the confidence region can be interpreted with a greater weight, since they represent a clearer indication of fatigue.

Figure 5:
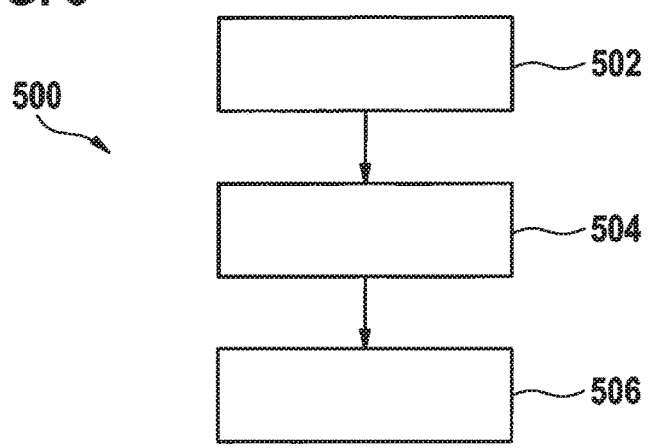
FIG. 5 is a flow chart of a method for recognizing fatigue, according to an exemplifying embodiment.

FIG. 5 is a flow chart of a method 500 for recognizing fatigue, according to an exemplifying embodiment. Method 500 can be executed, for example, on an apparatus as depicted in FIG. 1. Method 500 has an ascertaining step 502, a determining step 504, and a comparing step 506. In ascertaining step 502, a first saccade and at least one further saccade of an eye movement of a person are ascertained using a gaze direction signal that models the eye movement. In determining step 504, a first data point representing a first amplitude of the first saccade and a first peak velocity of the first saccade, and at least one further data point representing a further amplitude of the further saccade and a further peak velocity of the further saccade, are determined using the gaze direction signal. In comparing step 506, the first data point and at least the further data point are compared with a saccade model. The person is recognized as fatigued if the data points have a predetermined relationship to a confidence region of the saccade model.

In other words, FIG. 5 is a flow chart of a method 500 for estimating the fatigue of a viewer based on recorded gaze angle information. In a classifying step 404 the gaze angle information is subdivided into saccadic and fixation portions; properties of the saccadic periods can also be determined, for example the magnitude or amplitude of the saccades and their peak velocity. This information is initially buffered until a number of data pairs are available. In a model creation step, the individual parameters of a model that correlates the saccade amplitude and the peak velocity are created using this data inventory. A second data inventory is constructed in order to identify changes in behavior with respect to the model. Comparing step 506 identifies how the data points present in the data inventory deviate from the expected distribution of the data points in accordance with the model. An interpreting step ascertains whether this deviation is sufficient to confirm a fatigue state.

If an exemplifying embodiment encompasses an "and/or" relationship between a first feature and a second feature, this is to be read to mean that the exemplifying embodiment according to one embodiment has both the first feature and the second feature, and according to a further embodiment has either only the first feature or only the second feature.

What is claimed is:

1. A method for recognizing fatigue of a driver of a vehicle, the method comprising:
    ascertaining, via an ascertaining device, a first saccade and at least one further saccade of an eye movement of a driver, using a gaze direction signal, received from an eye detection device, that models the eye movement;
    determining, via a determining device, a first data point representing a first amplitude of the first saccade and a first peak velocity of the first saccade, and at least one further data point representing a further amplitude of the further saccade and a further peak velocity of the further saccade, using the gaze direction signal;
    comparing, via a comparing device, the first data point and at least the further data point with a saccade model, wherein the driver is recognized as fatigued if the first and further data points have a predetermined relationship to a confidence region of the saccade model; and
    providing a fatigue signal, if the driver is recognized as fatigued, to at least one of provide a warning to the driver and prompting the driver to rest.

2. The method as recited in claim 1, further comprising:
    personalizing the saccade model to the driver, wherein at least one parameter of the saccade model is determined using the first and further data points that represent temporally previous data points.

3. The method as recited in claim 2, wherein in the personalizing task, the saccade model is personalized using the first and further data points as a predetermined minimum number of data points.

4. The method as recited in claim 2, wherein in the personalizing task, the first and further data points are from a predefined time window.

5. The method as recited in claim 1, wherein in the comparing task, the driver is recognized as fatigued if a predetermined proportion of the first and further data points lie outside the confidence region.

6. The method as recited in claim 1, wherein in the comparing task, the first and further data points are weighted.

7. The method as recited in claim 1, wherein in the determining task, additional data points of the saccades, representing the amplitude of the saccade and a duration of the saccade, are determined using the gaze direction signal, the comparing task being performed using the additional data points.

8. The method as recited in claim 1, wherein in the comparing task, the saccade model is based on the following equation:

$$V_p = V_m(1 - e^{-A/C}),$$

where
    $V_p$ represents the peak velocity, $V_m$ and $C$ represent person-specific parameters, and $A$ represents the amplitude.

9. An apparatus for recognizing fatigue of a driver of a vehicle, comprising:
    an ascertaining device for ascertaining a first saccade and at least one further saccade of an eye movement of a driver, using a gaze direction signal, received from an eye detection device, that models the eye movement;
    a determining device for determining a first data point representing a first amplitude of the first saccade and a first peak velocity of the first saccade, and at least one further data point representing a further amplitude of the further saccade and a further peak velocity of the further saccade, using the gaze direction signal; and
    a comparing device for comparing the first data point and at least the further data point with a saccade model, wherein the driver is recognized as fatigued if the first and further data points have a predetermined relationship to a confidence region of the saccade model;
    wherein a fatigue signal is provided, if the driver is recognized as fatigued, to at least one of provide a warning to the driver and prompt the driver to rest.

10. The apparatus as recited in claim 9, wherein the saccade model is personalized to the driver, wherein at least one parameter of the saccade model is determined using the first and further data points that represent temporally previous data points.

11. The apparatus as recited in claim 10, wherein the saccade model is personalized using the first and further data points as a predetermined minimum number of data points.

12. The apparatus as recited in claim 10, wherein in the personalizing, the first and further data points are from a predefined time window.

13. The apparatus as recited in claim 9, wherein in the comparing, the driver is recognized as fatigued if a predetermined proportion of the first and further data points lie outside the confidence region.

14. The apparatus as recited in claim 9, wherein in the comparing, the first and further data points are weighted.

15. The apparatus as recited in claim 9, wherein additional data points of the saccades, representing the amplitude of the saccade and a duration of the saccade, are determined using the gaze direction signal, the comparing being performed using the additional data points.

16. The apparatus as recited in claim 9, wherein in the comparing, the saccade model is based on the following equation:

$$V_p = V_m(1-e^{-A/C}),$$

where
$V_p$ represents the peak velocity, $V_m$ and $C$ represent person-specific parameters, and $A$ represents the amplitude.

17. A non-transitory computer readable medium having a computer program, which is executable by a processor, comprising:
a program code arrangement having program code for recognizing fatigue of a driver of a vehicle, by performing the following:
ascertaining, via an ascertaining device, a first saccade and at least one further saccade of an eye movement of a driver, using a gaze direction signal, received from an eye detection device, that models the eye movement;
determining, via a determining device, a first data point representing a first amplitude of the first saccade and a first peak velocity of the first saccade, and at least one further data point representing a further amplitude of the further saccade and a further peak velocity of the further saccade, using the gaze direction signal; and
comparing, via a comparing device, the first data point and at least the further data point with a saccade model, wherein the driver is recognized as fatigued if the first and further data points have a predetermined relationship to a confidence region of the saccade model; and
providing a fatigue signal, if the driver is recognized as fatigued, to at least one of provide a warning to the driver and prompting the driver to rest.

18. The computer readable medium as recited in claim 17, further comprising:
personalizing the saccade model to the driver, wherein at least one parameter of the saccade model is determined using the first and further data points that represent temporally previous data points.

19. The computer readable medium as recited in claim 18, wherein in the personalizing task, the saccade model is personalized using the first and further data points as a predetermined minimum number of data points.

20. The computer readable medium as recited in claim 18, wherein in the personalizing task, the first and further data points are from a predefined time window.

21. The computer readable medium as recited in claim 17, wherein in the comparing task, the driver is recognized as fatigued if a predetermined proportion of the first and further data points lie outside the confidence region.

22. The computer readable medium as recited in claim 17, wherein in the comparing task, the first and further data points are weighted.

23. The computer readable medium as recited in claim 17, wherein in the determining task, additional data points of the saccades, representing the amplitude of the saccade and a duration of the saccade, are determined using the gaze direction signal, the comparing task being performed using the additional data points.

24. The computer readable medium as recited in claim 17, wherein in the comparing task, the saccade model is based on the following equation:

$$V_p = V_m(1-e^{-A/C}),$$

where
$V_p$ represents the peak velocity, $V_m$ and $C$ represent person-specific parameters, and $A$ represents the amplitude.

* * * * *